(12) United States Patent
Wong et al.

(10) Patent No.: US 9,932,635 B2
(45) Date of Patent: Apr. 3, 2018

(54) METHOD FOR EXOSOMAL BIOMARKER DETECTION BY ELECTRIC FIELD-INDUCED RELEASE AND MEASUREMENT

(75) Inventors: David T. Wong, Beverly Hills, CA (US); Fang Wei, North Hills, CA (US); Wei Liao, North Hills, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 441 days.

(21) Appl. No.: 14/119,843

(22) PCT Filed: May 24, 2012

(86) PCT No.: PCT/US2012/039471
§ 371 (c)(1),
(2), (4) Date: Jun. 20, 2014

(87) PCT Pub. No.: WO2012/162563
PCT Pub. Date: Nov. 29, 2012

(65) Prior Publication Data
US 2014/0315195 A1  Oct. 23, 2014

Related U.S. Application Data

(60) Provisional application No. 61/489,634, filed on May 24, 2011.

(51) Int. Cl.
*C12Q 1/68* (2006.01)
*C12N 15/10* (2006.01)
(Continued)

(52) U.S. Cl.
CPC ....... *C12Q 1/6881* (2013.01); *C12N 15/1013* (2013.01); *C12Q 1/6806* (2013.01);
(Continued)

(58) Field of Classification Search
CPC ............... C12Q 1/6881; C12Q 1/6806; C12N 15/1013; G01N 33/56966; G01N 33/5005;
(Continued)

(56) References Cited

U.S. PATENT DOCUMENTS 7,598,064 B2    10/2009 Lee et al.
9,629,929 B2 *   4/2017 Lotvall ................ C12N 15/113
(Continued)

FOREIGN PATENT DOCUMENTS

WO    WO 2007/126386 A1    11/2007
WO    WO2009/017878    *   2/2009
(Continued)

OTHER PUBLICATIONS

Bahi, M. et al., Electroporation and lysis of marine microalga Karenia brevis for RNA extraction and amplification. J. R. Soc. Interface, vol. 8, pp. 601-608 (2010).
(Continued)

*Primary Examiner* — Melanie Yu Brown
(74) *Attorney, Agent, or Firm* — Morgan, Lewis & Bockius LLP; Jeffry S. Mann (57) ABSTRACT

The molecules harbored in exosomes play important roles in biological science. A highly desirable goal for exosome research is the rapid, simple, simultaneous tracking and quantification of exosome harbored molecules. Disclosed herein are methods and devices for inducing the release and measurement of biomolecules harbored in exosomes. The disclosed method, Electric Field Induced Release and Measurement (EFIRM) technique, uses an electrical field to simultaneously disrupt exosomes to release the contents and measure the harbored exosomal RNA/proteins. The exosome vesicle contents can be released within minutes. This provides a potential on-site method for the detection of exosome-harbored biomolecules.

18 Claims, 5 Drawing Sheets

(51) Int. Cl.
G01N 33/50 (2006.01)
G01N 33/543 (2006.01)
G01N 33/569 (2006.01)
G01N 33/49 (2006.01)

(52) U.S. Cl.
CPC ..... G01N 33/5005 (2013.01); G01N 33/5076 (2013.01); G01N 33/54326 (2013.01); G01N 33/56966 (2013.01); G01N 33/49 (2013.01)

(58) Field of Classification Search
CPC ......... G01N 33/5076; G01N 33/54326; G01N 33/49
See application file for complete search history.

(56) References Cited

U.S. PATENT DOCUMENTS

| | | | |
|---|---|---|---|
| 2004/0009529 A1* | 1/2004 | Weimer | G01N 33/5304 435/7.1 |
| 2007/0125650 A1* | 6/2007 | Scurati | B03C 5/026 204/547 |
| 2009/0220944 A1 | 9/2009 | Stephano et al. | |
| 2010/0018046 A1 | 1/2010 | Pollabauer | |
| 2010/0184046 A1* | 7/2010 | Klass | C12Q 1/6886 435/7.1 |

FOREIGN PATENT DOCUMENTS

| | | |
|---|---|---|
| WO | WO 2010/119256 A1 | 10/2010 |
| WO | WO 2010/141862 A2 | 12/2010 |

OTHER PUBLICATIONS

Caby MP et al., Exosomal-like vesicles are present in human blood plasma. Int Immunol 17, pp. 879-887 (2005).
Chen T-H, Wei F, & Ho CM, Near-field ion flow for molecular scale manipulation. Solid-State Sensors, Actuators and Microsystems Conference Transducers. International 421-424 (2009).
Chen C et al., Microfluidic isolation and transcriptome analysis of serum microvesicles. Lab Chip 10, pp. 505-511 (2010).
Denzer K,. et al., Exosome: from internal vesicle of the multivesicular body to intercellular signaling device. J Cell Sci 113 Pt 19, pp. 3365-3374 (2000).
Fevrier B & Raposo G, Exosomes: endosomal-derived vesicles shipping extracellular messages. Current Opinion in Cell Biology 16, pp. 415-421 (2004).
Gibbings DJ et al., Multivesicular bodies associate with components of miRNA effector complexes and modulate miRNA activity. Nat Cell Biol 11, pp. 1143-1149 (2009).
Gonzalez-Begne M. et al., Proteomic analysis of human parotid gland exosomes by multidimensional protein identification technology (MudPIT). J Proteome Res 8, pp. 1304-1314 (2009).
Han, F. et al., Fast Electrical Lysis of Cells for Capillary Electrophoresis. Anal. Chem. vol. 75, pp. 3688-3696 (2003).
Houseley J, RNA-quality control by the exosome. Nature Reviews Molecular Cell Biology 7, pp. 529-539 (2006).
Johansson SM, Exosome-like vesicles in human breast milk. Journal of Immunology 176, S184-S184 (2006).
Kesimer M. et al., Characterization of exosome-like vesicles released from human tracheobronchial ciliated epithelium: a possible role in innate defense. FASEB J 23, pp. 1858-1868 (2009).
Kim, J. et al., Microfluidic sample preparation: cell lysis and nucleic acid purification. Critical Review, Integr. Biol., vol. 1, pp. 574-586 (2009).
Liu CH et al., Electrodynamically actuated on-chip flow cytometry with low shear stress for electro-osmosis based sorting using low conductive medium. Microelectronic Engineering 87, pp. 2582-2591 (2010).
Lu, H. et al., A microfluidic electroporation device for cell lysis, Lab Chip, vol. 5, pp. 23-29 (2005).
Miranda KC et al., Nucleic acids within urinary exosomes/microvesicles are potential biomarkers for renal disease. Kidney International 78, pp. 191-199 (2010).
Ogawa Y. et al., Exosome-like vesicles with dipeptidyl peptidase IV in human saliva. Biol Pharm Bull 31, pp. 1059-1062 (2008).
Palanisamy V. et al., Nanostructural and Transcriptomic Analyses of Human Saliva Derived Exosome. Plos One 5, (2010).
Park NJ et al., Characterization of RNA in saliva. Clin. Chem. 52, pp. 988-994 (2006).
Park NJ et al., Salivary microRNA: discovery, characterization, and clinical utility for oral cancer detection. Clin Cancer Res 15, pp. 5473-5477 (2009).
Pisitkun T, Shen RF, & Knepper MA, Identification and proteomic profiling of exosomes in human urine. Proc Natl Acad Sci U S A 101, pp. 13368-13373 (2004).
Pohl, H., Some Effects of Nonuniform Fields on Dielectrics. Journal of Applied Physics, vol. 29, No. 8, pp. 1182-1188 (1958).
Raimondo, F. et al., Advances in membranous vesicle and exosome proteomics improving biological understanding and biomarker discovery. Proteomics, vol. 11, pp. 709-720 (2011).
Rosell R et al., Circulating MicroRNA Signatures of Tumor-Derived Exosomes for Early Diagnosis of Non-Small-Cell Lung Cancer. Clinical Lung Cancer 10, pp. 8-9 (2009).
Schmid M & Jensen TH,The exosome: a multipurpose RNA-decay machine. Trends in Biochemical Sciences 33, pp. 501-510 (2008).
Schorey JS & Bhatnagar S., Exosome function: From tumor immunology to pathogen biology. Traffic 9, pp. 871-881 (2008).
Sharma S. et al., Structural-mechanical characterization of nanoparticle exosomes in human saliva, using correlative AFM, FESEM, and force spectroscopy. ACS Nano 4, pp. 1921-1926 (2010).
Smalheiser NR, Exosomal transfer of proteins and RNAs at synapses in the nervous system. Biology Direct 2 (2007).
Stoorvogel W et al., The biogenesis and functions of exosomes. Traffic 3, 321-330 (2002).
Suehiro, J. et al., Selective detection of bacteria by a dielectrophoretic impedance measurement method using an antibody-immobilized electrode chip. Sensors and Actuators B., vol. 199, No. 1, pp. 319-326 (2006).
Sugioka H., Asymmetrical reverse vortex flow due to induced-charge electro-osmosis around carbon stacking structures. Physical Review E 83 Abstract(2011).
Taylor DD & Gercel-Taylor C., MicroRNA signatures of tumor-derived exosomes as diagnostic biomarkers of ovarian cancer., Gynecologic Oncology, vol. 110, pp. 13-21 (2008).
Valadi H. et al., Exosome-mediated transfer of mRNAs and microRNAs is a novel mechanism of genetic exchange between cells. Nature Cell Biology 9, pp. U654-U672 (2007).
van Niel G, Exosomes: A common pathway for a specialized function. Journal of Biochemistry 140, 13-21 (2006).
Wei F. et al. Electrochemical sensor for multiplex biomarkers detection. Clin Cancer Res 15, pp. 4446-4452 (2009).
Wei F. et al., Electric potential induced dissociation of hybridized DNA with hairpin motif immobilized on silicon surface. Langmuir 22, pp. 6280-6285 (2006).
Wei F. et al., Bio/abiotic interface constructed from nanoscale DNA dendrimer and conducting polymer for ultrasensitive biomolecular diagnosis. Small 5, pp. 1784-1790 (2009).
Wong PK et al., Electrokinetics in micro devices for biotechnology applications. Ieee-Asme Transactions on Mechatronics 9, pp. 366-376 (2004).
Wubbolts R. et al., Proteomic and biochemical analyses of human B cell-derived exosomes. Potential implications for their function and multivesicular body formation. J Biol Chem 278, pp. 10963-10972 (2003).

* cited by examiner

METHOD FOR EXOSOMAL BIOMARKER DETECTION BY ELECTRIC FIELD-INDUCED RELEASE AND MEASUREMENT

CROSS-REFERENCES TO RELATED APPLICATIONS

This application claimed priority benefit of U.S. provisional patent application Ser. No. 61/489,634 filed May 24, 2011, the disclosure of which is incorporated by reference in its entirety.

STATEMENT OF GOVERNMENT RIGHTS

This invention was made with Government support under Grant No. DE017790, awarded by the National Institutes of Health. The Government has certain rights in this invention.

BACKGROUND

Exosomes are lipid-encapsulated vesicles that are released by various cells into body fluids, including blood, urine, milk, saliva and cerebrospinal fluid. Fevrier B & Raposo G (2004) *Current Opinion in Cell Biology* 16, 415-421, Taylor D D, Gercel-Taylor C (2010) *Gynecologic Oncology* 116, 153-153, Pisitkun T, Shen R F, Knepper M A (2004) *Proc Natl Acad Sci USA* 101, 13368-13373, Miranda K C, Bond D T, McKee M, Skog J, Paunescu T G, Da Silva N, Brown D, Russo L M (2010) *Kidney International* 78, 191-199, Johansson S M, Admyre C, Rahman Q K, Filen J J, Lahesmaa R, Norman M, Neve E, Scheynius A Gabrielsson S (2006) *Journal of Immunology* 176, S184-S184, Sharma S, Rasool H I, Palanisamy V, Mathisen C, Schmidt M, Wong D T, Gimzewski J K (2010) *ACS Nano* 4, 1921-1926, Palanisamy V, Sharma S, Deshpande A, Zhou H, Gimzewski J, Wong D T (2010) *Plos One* 5(1): e8577. Exosomes contain various bio-molecules of their cell of origin, including proteins and RNA molecules. By remote communication via the harbored bio-molecules, exosomes regulate a variety of cellular pathways in recipient cells that relate to the progression and prognosis of disease conditions. Smalheiser N R (2007) *Biology Direct* 2:35, van Niel G, Porto-Carreiro I, Simoes S, Raposo G (2006) *Journal of Biochemistry* 140:13-21, Gibbings D J, Claudo C, Erhardt M, Voinnet O (2009) *Nat Cell Biol* 11: 1143-1149, Schorey J S, Bhatnagar S (2008) *Traffic* 9:871-881. Exosome research, based on detection of encapsulated biomarkers, has shown great potential in disease therapeutics and diagnostics. Rosell R, Wei J, Taron M (2009) *Clinical Lung Cancer* 10, 8-9.

Unfortunately, the vesicle structure of exosomes hinders the detection of exosome-harbored bio-molecules. The particular lipid composition of the vesicle and the presence of the harbored protein, nucleic acid, and other constituents confer protection to the vesicle against degradation and contribute to its stability in the extracellular environment. Schmid M, Jensen T H (2008) *Trends in Biochemical Sciences* 33:501-510; Houseley J, LaCava J, Tollervey D (2006) *Nature Reviews Molecular Cell Biology* 7:529-539.

A method for releasing the exosome encapsulated constituents for analysis is to apply lysis reagents. The lysis reaction time typically varies from several minutes to several hours and can compromise the integrity of the bio-molecules. Therefore, for translational and clinical applications, a need exists for rapid exosome-specific extraction and highly sensitive, specific detection of exosome associated bio-molecules. These and other needs are addressed by the methods and devices disclosed herein.

BRIEF DESCRIPTION OF THE DRAWINGS

FIG. 3 depicts a comparison between electric field (E-field) and Triton X-100 lysis for releasing exosomal GAPDH mRNA from human saliva. Control groups were not treated with the E-field or Triton X-100, but were incubated for the same time period. a) Schematic illustration of an exosome disrupted with E-field and RNA released. b) TEM images before (left) and after (right) E-field (top) or Triton X-100 (bottom) treatment. (i and iii) Exosomes (arrows) attached to anti-hCD63 magnetic beads; (ii and iv) Exosomes were disrupted after treating with (ii) a cyclic square wave (csw) E-field for 200 s, or (iv) with Triton-X 100 for 20 min. The background is the lacey support film for TEM. c) GAPDH mRNA was measured by EFIRM after csw E-field (top) or Triton X-100 (bottom) treatment. Measurements of released RNA (filled bars) are presented as the ratio between the mRNA signal and the blank control (casein PBS buffer with no exosomes). Positive controls (without [w/o] electrical field treatment in the release step, open bars) were undegraded mRNA measured in untreated exosome samples; therefore, these mRNAs were not exposed to saliva enzymes.

SUMMARY OF THE INVENTION

The rapid degradation of released bio-molecules implicates a need for detection technologies that can make accurate assessments within seconds to minutes. For example, mRNA levels were reduced to less than 40% within 1 minute of release from macromolecules into saliva. Park NJ, Li Y, Yu TW, Brinkman BMN, Wong DT (2006) *Clin. Chem.* 52: 988-994. Stabilization reagents are therefore necessary for accurate exosome biomarker detection. The combination of exosome releasing agents and stabilization reagents renders the process complicated and may introduce interference.

An electric field, particularly one with a non-uniform profile, can stimulate vesicle deformation in biological samples, and it can direct the flow of the released bio-molecules. Wei F, Qu P, Zhai L, Chen C, Wang H, Zhao X S (2006) *Langmuir* 22:6280-6285; Wei F, Liao W, Xu Z, Yang Y, Wong D T, Ho C M (2009) *Small* 5:1784-1790. An electric field can cause redistribution or polarization of lipid vesicular structures that protect bio-molecules. The non-uniform electrical field will either rupture the membrane or disrupt the tertiary structure of the exosomal lipid bilayer, which causes temporary pore formation; in both cases, the harbored bio-molecules can be released.

Accordingly, disclosed herein are methods and devices for directly detecting bio-molecules associated with the exosome by electrical field-induced release and measurement.

In one aspect, the present disclosure provides a method for detecting a biomarker present in an exosome, the method comprising: providing a biological fluid comprising exosomes; extracting exosomes from the biological fluid to form an enriched exosome composition; contacting the enriched exosome composition with a detection reagent that specifically binds to the biomarker; applying an electrical field to the enriched exosome composition in the presence of the detection reagent; detecting an interaction between the biomarker and the detection reagent.

In one aspect, the present disclosure provides a method for detecting a biomarker present in an exosome, the method comprising: providing a biological fluid comprising exosomes; contacting the biological fluid with an exosome extraction reagent to form a complex between the exosome and the exosome extraction reagent, the exosome extraction reagent comprising a first affinity moiety bound to a magnetic bead, wherein the first affinity binding moiety specifically binds to a surface-exposed exosome marker; separating the complex formed between the exosome and the exosome extraction reagent from the biological fluid; contacting a solid phase with the complex formed between the exosome and the exosome extraction reagent, the solid phase comprising a first contact region under the influence of a magnetic field, a second contact region, and a detection reagent immobilized at the second contact region, the detection reagent comprising a second affinity moiety that specifically binds to the biomarker; immobilizing the complex formed between the exosome and the exosome extraction reagent at the first contact region; applying an electrical field to the immobilized complex formed between the exosome and the exosome extraction reagent at the first contact region; and detecting an interaction between the biomarker and the detection reagent.

In some embodiments of the methods described above, the biomarker is a protein.

In some embodiments of the methods described above, the biomarker is a nucleic acid. In a specific embodiment, the nucleic acid is an mRNA.

In some embodiments of the methods described above, the biological fluid is selected from the group consisting of saliva, whole blood, blood plasma, blood serum, amniotic fluid, bile, colostrum, breast milk, cerebrospinal fluid (CSF), lymph, gastric acid, nasal mucus, pleural fluid, semen, tears, and urine. In a specific embodiment, the biological fluid is saliva. In another specific embodiment, the biological fluid is whole blood, blood plasma, or blood serum.

In some embodiments of the methods described above, the step of extracting exosomes from the biological fluid comprises: contacting the biological fluid with an exosome extraction reagent that specifically binds to a surface-exposed exosome marker to form a complex between the exosome and the exosome extraction reagent; and separating the complex formed between the exosome and the exosome extraction reagent from the biological fluid.

In some embodiments of the methods described above, the surface-exposed exosome marker is CD63.

In some embodiments of the methods described above, the exosome extraction reagent comprises an antibody.

In some embodiments of the methods described above, the exosome extraction reagent comprises an exosome-specific lectin.

In some embodiments of the methods described above, the exosome extraction reagent comprises a bead attached to a first affinity moiety that specifically binds to a surface-exposed exosome marker. In a specific embodiment, the bead is a magnetic bead.

In some embodiments of the methods described above, the detection reagent comprises a second affinity moiety immobilized to a solid phase, wherein the second affinity moiety specifically binds to the biomarker.

In some embodiments of the methods described above, the second affinity moiety comprises an antibody.

In some embodiments of the methods described above, the second affinity moiety comprises a nucleic acid.

In some embodiments of the methods described above, the solid phase comprises an electrochemical sensor. Non-limiting examples of electrochemical sensors are described in U.S. Patent Application Publication No. 2010/0330706, the content of which is hereby incorporated herein by reference in its entirety for all purposes.

In some embodiments of the methods described above, the absolute value of the maximum voltage of the electric field does not exceed 1 volt (V).

In some embodiments of the methods described above, the absolute value of the maximum voltage of the electric field does not exceed 500 millivolt (mV).

In yet other embodiments of the methods described above, the absolute value of the maximum voltage of the electric field does not exceed 3.0 V, 2.5 V, 2.0 V, 1.5 V, 1.4 V, 1.3 V, 1.2 V, 1.1 V, 1.0 V, 0.9 V, 0.8 V, 0.7 V, 0.6 V, 0.5 V, 0.4 V, 0.3 V, or 0.2 V.

In some embodiments of the methods described above, the electric field is applied for less than 300 seconds.

In some embodiments of the methods described above, the electric field is applied for 200±30 seconds.

In yet other embodiments of the methods described above, the electric field is applied for 60±30 seconds, 90±30 seconds, 120±30 seconds, 150±30 seconds, 180±30 seconds, 210±30 seconds, 240±30 seconds, 270±30 seconds, 300±30 seconds, 330±30 seconds, 360±30 seconds, 390±30 seconds, 420±30 seconds, 450±30 seconds, 480±30 seconds, 510±30 seconds, 540±30 seconds, 570±30 seconds, 600±30 seconds, or more seconds.

In some embodiments of the methods described above, the electric field is a non-uniform electric field.

In some embodiments of the methods described above, the non-uniform electric field is a cyclic square wave electrical field (csw E-field).

In some embodiments of the methods described above, the csw E-field comprises 15 cycles of −300±50 mV for 9±2 seconds followed by 200±50 mV for 1±0.5 second.

In some embodiments of the methods described above, the csw E-field comprises 20 cycles of −300 mV for 9 seconds followed by 200 mV for 1 second.

In one aspect, the present disclosure provides a method for analyzing exosome biomolecules, the method comprising: providing an exosome sample; and applying an electrical field to the exosome sample, such that the exosome no longer excludes the extra-membrane environment; and thereby analyzing exosome biomolecules.

In some embodiments of the methods described above, the method further comprises applying a magnetic force prior to applying the electric field.

In some embodiments of the methods described above, the electric field is a cyclic square wave.

In some embodiments of the methods described above, the electric filed is less than 1 volt.

In some embodiments of the methods described above, the electric field is less than 500 milli-Volts.

In some embodiments of the methods described above, the electric filed is applied for 200 seconds or less.

In some embodiments of the methods described above, the electric field is a non-uniform electric field.

In some embodiments of the methods described above, the exosomes are isolated from saliva.

In some embodiments of the methods described above, the saliva is human saliva.

In some embodiments of the methods described above, the exosome is bound by an antibody.

In some embodiments of the methods described above, the antibody is attached to a magnetic bead.

In some embodiments of the methods described above, the biomolecules is a polypeptide and/or a nucleic acid.

In some embodiments of the methods described above, the nucleic acid is a ribonucleic acid.

In some embodiments of the methods described above, the polypeptide is an integral exosomal membrane protein.

In one aspect, the present disclosure provides a method for releasing an encapsulated biomolecule comprising applying an electrical field to an encapsulated biomolecule, wherein the biomolecule is encapsulated in an encapsulating structure and wherein the electrical field is sufficient to cause the encapsulating structure to degrade sufficiently so as to release the encapsulated biomolecule and wherein the electrical field is a cycle square wave.

DETAILED DESCRIPTION

Biological assay systems are important in biotechnology and medical diagnostics. A useful biological agent detection method is using DNA or RNA detection through a polymerase chain reaction (PCR), real-time polymerase chain reaction (RT-PCR), or reverse-transcriptase polymerase chain reaction. Alternatively, assaying for the presence of a particular protein can also be used to detect or study biological samples of interest. Before a biological sample can be analyzed using PCR or protein detection methods, it must first be prepared for analysis. A challenge in biological sample preparation is lysis.

Lysis methods can be generally divided into reagent-assisted or reagent-less lysis methods. The former uses lytic agents such as detergent to lyse cells. However, these lytic reagents can interfere following analysis process and the system can be overly complicated due to lytic agent injection and sample rinsing step. Therefore, reagentless lysis methods have been developed with various approaches.

Reagentless lysis methods can be largely categorized as mechanical (Carlo, D. D., Joeng, K., Lee, L. P. (2003) *Lab Chip* 3:287, thermal (Lie, R. H., Yang, J., Lenigk, R., Bonanno, J., Grodzinski, P. (2004) *Anal. Chem.* 76:1824; Waters, L. C., Jacobson, S. C., Kroutchinina, N., Khandurina, J., Foote, J. M., Ramsey, J. M. (1998) *Anal. Chem.* 70-158) and electrical (Lee, S. and Tai, Y. (1999) *Sensors and Actuators A.* 73:74-79; Lu, H., Schmidt, M. A., Jensen, K. F. (2005) *Lab Chip* 5:23; Lee, D. W. and Cho, Y. H. (2006) Micro Electro Mechanical Systems Conference, Istanbul, page 426; Wang, H. Y., Bhunia, A. K., Lu, C. (2006) *Biosens. Bioelectron.* 22:582).

Mechanical lysis uses a crushing or grinding action to cleave cell membranes or a sharp object to pierce the cell membrane. For example, glass beads can be centrifuged along with the sample at a high angular velocity, cleaving cells as they grind past each other. Some centrifuge systems also rock the sample using three dimensional movements to increase the efficiency of lysis. Another method of mechanical lysis is to pressure the cell sample and flow it past a piercing object at a high velocity. However, in mechanical lysis methods, the size of the sharp structures should be decreased as the sample size decreases. Moreover, the fabrication process can be challenging, and costly.

The thermal lysis methods are using high temperature (~94'C) to lyse the cell. Heating cells to a high temperature causes cellular protein denaturation and cell membrane breakdown. This method is not ideal because the harsh process of thermal lysis may destroy the target to be detected.

Electrical lysis methods are usually based on the irreversible electroporation of the lipid bilayer of the target particles. Electrical lysis methods do not possess the drawbacks inherent in mechanical and thermal lysis methods.

While electrical lysis has been applied to mammalian cells, bacteria and viruses (Park, K., Akin, D., Bashir, R. (2007) *Biomed Microdevices* 9:877-883), it was unknown whether electrical lysis could be applied to exosomes and for exosome analysis before the instant disclosure.

Accordingly, in some embodiments, a method of electrical lysis of an exosome and collection of at least a portion of contents thereof is provided. The method entailing applying an alternating electrical current to an exosome such that the exosome is lysed and collecting at least a portion of the contents thereof.

In order for the present disclosure to be more readily understood, certain terms and phrases are defined below as well as throughout the specification.

DEFINITIONS

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3rd ed., J. Wiley & Sons (New York, N.Y. 2001); March, *Advanced Organic Chemistry Reactions, Mechanisms and Structure 5th ed.*, J. Wiley & Sons (New York, N.Y. 2001); and Sambrook and Russell, *Molecular Cloning: A Laboratory Manual* 3rd ed., Cold Spring harbor Laboratory Press (Cold Spring Harbor, N.Y. 2001), provide one skilled in the art with a general guide to many terms used in the present disclosure. As appropriate, procedures involving the use of commercially available kits and reagents are generally carried out in accordance with manufacturer defined protocols and/or parameters unless otherwise noted.

As used herein, the terms "exosome" and "luminal vesicle" are used interchangeably to refer to a small membrane vesicle having a diameter between about 40-100 nm in diameter present in biological fluids. Exosomes are released by various cell types (e.g., tumor cells, neurons, B- and T-lymphocytes, and intestinal epithelial cells) into the extracellular environment, e.g., various biological fluids. Briefly, this occurs when late endosomes (multivesicular bodies) fuse with the plasma membrane and are released from the cell.

"Exosome contents" or "contents of the exosome" refer to the polynucleotides, polypeptides, hormones and organic and inorganic molecules found within the lipid membrane of the exosome. Exosomes are described below, in the section entitled "Exosome." Examples of polynucleotides found within the exosome include, without limitation, DNA and RNA as describe above.

As used herein, the term "enriched exosome sample" refers to a sample containing exosomes isolated or extracted from a biological sample or fluid. Methods for extracting, exosomes from biological fluids are well known in the an and include, without limitation, centrifugation, differential centrifugation, ultracentrifugation, precipitation, and affinity capture.

As used herein, the terms "biomarker present in an exosome" or "biomarker" are used interchangably to refer to a molecule attached to the surface, embedded within, or encapsulated within an exosome present in a biological fluid. In certain embodiments, the biomarker is a polypeptide (e.g., a protein or peptide), nucleic acid (e.g., DNA, RNA, mRNA, tRNA, or rRNA), lipid, or carbohydrate moiety. In certain embodiments, the biomarker is present at a higher or lower concentration in an exosome present in an individual with a particular disease or condition, as compared to the level of the biomarker in an exosome present in an individual who does not have the particular disease or condition. Biomarkers generally refer to a gene, mRNA, protein that is present in a biological sample, which is useful for the diagnosis of a disease, for providing a prognosis, or for preferential targeting of a pharmacological agent to an affected cell or tissue.

As used herein, the term "affinity moiety" refers to a binding molecule (e.g., antibody, aptamer, peptide, or nucleic acid) that specifically binds to a particular target molecule (e.g., a biomarker present in an exosome or a marker present on the surface of an exosome).

As used herein, the term "exosome extraction reagent" refers to an agent comprising an affinity moiety (e.g., an antibody, aptamer, peptide, or nucleic acid) that specifically binds to a marker present in the surface of an exosome (e.g., a polypeptide, nucleic acid, lipid, or carbohydrate moiety). Exosome extraction reagents may further include, for example, a solid phase onto which the affinity reagent is immobilized (for example: a bead such as a magnetic bead, a chip, a strip, or a surface such as a well in a microtitre plate). In one embodiment, the marker present in the surface of an exosome is CD63. Other, non-limiting, examples of markers found on the surface of exosomes are described in Théry C. et al. (Nat Rev Immunol. 2002 August; 2(8):569-79), the content of which is hereby incorporated herein by reference in its entirety for all purposes.

As used herein, the term "detection reagent" refers to an agent comprising an affinity moiety (e.g., an antibody, aptamer, peptide, or nucleic acid) that specifically binds to a biomarker present in an exosome (e.g., a polypeptide, nucleic acid, lipid, or carbohydrate moiety). Detection reagents may further include, for example, a detectable moiety (e.g., a radioisotope, a fluorescent label, a magnetic label, an enzyme, or a chemical moiety such as biotin or digoxigenin). The detectable moiety can be detected directly, or indirectly, by the use of a labeled specific binding partner of the detectable moiety. Alternatively, the specific binding partner of the detectable moiety can be coupled to an enzymatic system that produces a detectable product. In one embodiment, the biomarker present in an exosome is CD9, CD63, CD81, CD82, or a combination therein. Other, non-limiting, examples of biomarkers present in an exosome are described in Théry C. et al. (Nat Rev Immunol. 2002 August; 2(8):569-79), the content of which is hereby incorporated herein by reference in its entirety for all purposes.

As used herein, the term "specifically binds" refers to a molecule that binds to a particular target molecule (e.g., a biomarker present in an exosome or a marker present on the surface of an exosome) with at least 2-fold greater affinity, as compared to a non-targeted molecule. In certain embodiments, a molecule specifically binds with at least 3-fold, 4-fold, 5-fold, 6-fold, 7-fold, 8-fold, 9-fold, 10-fold, 25-fold, 50-fold, 100-fold, 500-fold, 1000-fold, 5000-fold, 10000-fold, or greater affinity, as compared to a non-targeted molecule.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides.

The term "gene" means the segment of DNA involved in producing a polypeptide chain. It may include regions preceding and following the coding region (leader and trailer) as well as intervening sequences (introns) between individual coding segments (exons).

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure. An isolated nucleic acid can be a component of an expression vector.

Purity is determined by any art-recognized method of analysis (e.g., band intensity on a stained gel, polyacrylamide gel electrophoresis, HPLC, mass-spectroscopy, or a similar means).

"Lysis" or to "lyse" refers to disrupting the integrity of a closed lipid membrane such that the contents of the closed lipid membrane are accessible and/or the contents are released into the extra-membrane environment. Using a cell as an example, lysis refers to causing the breaking of the cellular membrane such that the contents of the cell are in direct contact with the extracellular milieu, A "lysate" is a liquid or solid collection of materials following a lysis procedure.

As used herein, the term "AC current" refers to an alternating electrical current that flows in one direction, reverses and flows in the opposite direction. As used herein, the term "DC current" refers to a direct electrical current that flows in one direction only. As used herein, the term "inverter" refers to an electrical device that converts DC current to AC current.

A "nonuniform electric field" refers to an electric field created by an electrical potential difference between two electrodes. The nonuniform electric field includes at least some electric field lines that are more locally concentrated at one electrode relative to the other electrode, e.g., more concentrated at the dispensing end relative to the second electrode or a grounded target surface. In some embodiments, the second electrode can be one or more ring electrodes, plate electrodes, and/or grounded target surfaces.

The term "square wave" is used herein as it is understood in the art, namely, a wave that is essentially in the form of an abrupt rise in value from a zero level followed by a period maintained at some maximum value followed by an abrupt decrease in value to the zero level. When plotting value against time, variations in the value produces a wave form made essentially of vertical and horizontal lines. Departures from absolutely vertical and horizontal lines through all portions of the wave are acceptable as long as the wave form of the electric field has an essentially square or rectangular form as understood by those skilled in the art.

As used herein, the terms "biological fluid" and "biological sample" are used interchangeably and refer to an extracellular sample from a patient. In certain embodiments, the biological sample is a biological fluid, while in other embodiments, the biological sample may be a non-fluid extracellular sample. Non-limiting examples of biological samples that can be used in the methods described herein include saliva, whole blood, blood plasma, blood serum, amniotic fluid, bile, colostrum, breast milk, cerebrospinal fluid (CSF), lymph, gastric acid, nasal mucus, pleural fluid, semen, tears, and urine As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

The term "differentially expressed" or "differentially regulated" refers generally to a protein or nucleic acid that is overexpressed (upregulated) or underexpressed (downregulated) in one biological sample compared to at least one other sample from a subject.

The terms "overexpress," "overexpression," "overexpressed," "upregulate," or "upregulated" interchangeably refer to a biomarker that is present at a detectably greater level in a biological sample in comparison to a biological sample from a control subject. Overexpression can be 10%, 20%, 30%, 40%, 50%, 60%, 70%, 80%, 90% or more in comparison to a sample from a control subject. In certain instances, overexpression is 1-fold, 2-fold, 3-fold, 4-fold 5, 6, 7, 8, 9, 10, or 15-fold or more higher levels of transcription and/or translation in comparison to a sample from a control subject.

The terms "underexpress," "underexpression," "underexpressed," "downregulate," or "downregulated" interchangeably refer to a biomarker that is present at a detectably lower level in a biological sample in comparison to a biological sample from a control subject. In certain instances, underexpression is 1-fold, 2-fold, 3-fold, 4-fold or more lower levels of transcription and/or translation in comparison to a control. Overexpression and underexpression can be detected using conventional techniques for detecting mRNA (e.g., RT-PCR, PCR, hybridization), proteins (e.g., ELISA, immunohistochemical techniques, mass spectroscopy, Luminex® xMAP technology), or microbes (e.g., microbial nucleic acid profiling).

Biological assay systems are important in biotechnology and medical diagnostics. A useful biological agent detection method is using DNA or RNA detection through a polymerase chain reaction (PCR), real-time polymerase chain reaction (RT-PCR), or reverse-transcriptase polymerase chain reaction. Alternatively, assaying for the presence of a particular protein can also be used to detect or study biological samples of interest. Before a biological sample can be analyzed using PCR or protein detection methods, it must first be prepared for analysis. A challenge in biological sample preparation is lysis.

Lysis methods can be generally divided into reagent-assisted or reagent-less lysis methods. The former uses lytic agents such as detergent to lyse cells. However, these lytic reagents can interfere following analysis process and the system can be overly complicated due to lytic agent injection and sample rinsing step. Therefore, reagentless lysis methods have been developed with various approaches.

In some embodiments, a method of electrical lysis of an exosome and collection of at least a portion of contents thereof is provided. The method entailing applying an alternating electrical current to an exosome such that the exosome is lysed and collecting at least a portion of the contents thereof.

Electrical Lysis

The application of electricity has been used to achieve lysis of viruses, prokaryotic and eukaryotic cells. However, whether electricity could be used to effectively lyse exosomes, and the conditions of such use, was unknown prior to the instant disclosure. Electrical lysis of cells has been demonstrated as a modification of various electroporation techniques.

Electroporation is a phenomenon that has been studied extensively. Weaver, J. C. *Journal of Cellular Biochemistry* (1993) 51:426-435; Rae, J. L.; Levis, R. A. *Eur. J Physiol.* (2002) 443, 664-670; Ho, S. Y.; Miltal, G. S. *Critical Rev. Biotech.* (1996) 16:349-362; Tsong, T. Y. *Biophys. J* (1991) 60:297-306; Bilska, A. Q.; DeRruin K. A.; Krassowska, W. *Bioelectrochemistry* (2000) 51:133-143; and Wilhelm, C; Winterhalter, M.; Zimmermann, U.; Benz, R. *Biophys. J.* (1993) 64:121-128. Multiple electrical pulses of a defined pulse width and voltage are used to induce a potential difference across the cell. When the transmembrane potential difference is large enough, pores are formed in the membrane which rapidly seal upon removal of the electric field. This process is widely used to load exogenous molecules into cells.

If the applied transmembrane voltage exceeds a critical value, pore formation becomes irreversible and cell lysis occurs. Some investigators have used this observation to move from electroporation to electrical lysis of cells, in one method, Cheng and coworkers reported the use of a pulsed, high voltage field of 20 second duration to lyse cells on a microfabricated device for a variety of applications including obtaining DNA and RNA from bacteria and the destruction of unwanted cells. Cheng, J., Sheldon, E X., Wu, L., Uribe, A., Cerrue, L. O., Carrino, J., Heller, M. J., O'Connell, J. P. *Nat. Biotech.* (1998) 16:541-546 and Cheng, Y., Sheldon, E., Wu, L., Heller, M. J., O'Connell, J. P. *Anal. Chem.* (1998) 70:2321-2326. These studies showed that combined AC fields for the study of membrane deformation or for dielectrophoretic separation of blood cells or *E. coli* cells, could also be used for cell lysis over a range of frequencies from 20 KHz to 1 MHz with potential differences of 40 to 2 kV/cm respectively. Krueger's studies of membrane deformation by electrical fields in the context of electroporation also reported cellular lysis with field strengths in this range. Krueger, M.; Thom F *Biophys J.* (1997) 73:2653-2666. Cheng et al. were able to achieve lysis of *E. coli* with several hundred bursts of an AC field of 500 volts each of 50 microseconds duration across an array o electrodes on a substrate with an inter electrode gap of about 200 microns. Cheng, J., Sheldon, E X., Wu, L., Uribe, A., Cerrue, L. O., Carrino, J., Heller, M. J., O'Connell, J. P. *Nat. Biotech.* (1998) 16:541-546.

Similarly, Lee and coworkers describe a micro-machined cell lysis device based on a similar theory. Lee, S. and Tai, Y. *Sensors and Actuators A*. (1999) 73:74-79. Ramsey and colleagues also utilized AC electrical fields for fast, high throughput lysis of cells on a microfluidic device followed by separation of the intracellular contents, [see McClain, M. A.; Culbertson, C. T.; Jacobson, S. C; Ramsey, J. M. *In Micro Total Analysis Systems* 2001; Ramsey, J. M.; van den Berg, A. Eds.; Kluwer Academic Publishers: London, 2001 pp. 301-302 and U.S. Pat. Publication No. 20030075446]. Yeung's group lysed a lymphocyte preloaded into a capillary with a 15-20 second exposure to an electric field from a Tesla coil. Lysis of the cell required 15-20 seconds by this method and the cell was also required to stick to the inner surface of the capillary. Xue, Q; Young. E. S. *Journal of Chromotogr. B.* (1996) 677:233-240.

Exosome

Exosomes are small vesicles that are released into the extracellular environment from a variety of different cells such as but not limited to, cells that originate from, or are derived from, the ectoderm, endoderm, or mesoderm including any such cells that have undergone genetic, environmental, and/or any other variations or alterations (e.g. Tumor cells or cells with genetic mutations). An exosome is typically created intracellularly when a segment of the cell membrane spontaneously invaginates and is ultimately exocytosed (see for example, Keller et al., Immunol. Lett. 107 (2): 102-8 (2006)).

Exosomes can have, but not be limited to, a diameter of greater than about 10, 20, or 30 nm. They can have a diameter of about 30-1000 nm, about 30-800 nm, about 30-200 nm, or about 30-100 nm. In some embodiments, the exosomes can have, but not be limited to, a diameter of less than about 10,000 nm, 1000 nm, 800 nm, 500 nm, 200 nm, 100 nm or 50 nm. As used throughout, the term "about," when referring to a value or to an amount is meant to encompass variations in some embodiments±10% from the specified amount, as such variations are appropriate.

Exosomes may also be referred to as microvesicles, nanovesicles, vesicles, dexosomes, bleb, blebby, prostasomes, microparticles, intralumenal vesicles, endosomal-like vesicles or exocytosed vehicles. As used herein, exosomes can also include any shed membrane bound particle that is derived from either the plasma membrane or an internal membrane. Exosomes can also include cell-derived structures bounded by a lipid bilayer membrane arising from both herniated evagination (blebbing) separation and sealing of portions of the plasma membrane or from the export of any intracellular membrane-bounded vesicular structure containing various membrane-associated proteins of tumor origin, including surface-bound molecules derived from the host circulation that bind selectively to the tumor-derived proteins together with molecules contained in the exosome lumen, including but not limited to tumor-derived microRNAs or intracellular proteins. Blebs and blebbing are further described in Charras et al., Nature Reviews Molecular and Cell Biology, Vol. 9, No. 11, p. 730-736 (2008). Exosomes can also include membrane fragments.

Circulating tumor-derived exosomes (CTEs) as referenced herein are exosomes that are shed into circulation or bodily fluids from tumor cells. CTEs, as with cell-of-origin specific exosomes, typically have unique biomarkers that permit their isolation from bodily fluids in a highly specific manner.

Exosomes can be directly assayed from the biological samples, such that the level of exosomes is determined or the one or more biomarkers of the exosomes are determined without prior isolation, purification, or concentration of the exosomes. Alternatively, exosomes may be isolated, purified, or concentrated from a sample prior to analysis.

In some embodiments, an exosome may be purified or concentrated prior to analysis. Analysis of an exosome can include quantitiating the amount one or more exosome populations of a biological sample. For example, a heterogeneous population of exosomes can be quantitated, or a homogeneous population of exosomes, such as a population of exosomes with a particular biomarker profile, a particular bio-signature, or derived from a particular cell type (cell-of-origin specific exosomes) can be isolated from a heterogeneous population of exosomes and quantitated. Analysis of an exosome can also include detecting, quantitatively or qualitatively, a particular biomarker profile or a bio-signature, of an exosome, as described below.

An exosome can be stored and archived, such as in a bio-fluid bank and retrieved for analysis as necessary. An exosome may also be isolated from a biological sample that has been previously harvested and stored from a living or deceased subject. In addition, an exosome may be isolated from a biological sample which has been collected as described in King et al., Breast Cancer Res 7(5): 198-204 (2005). An exosome may be isolated from an archived or stored sample. Alternatively, an exosome may be isolated from a biological sample and analyzed without storing or archiving of the sample. Furthermore, a third party may obtain or store the biological sample, or obtain or store the exosomes for analysis.

An enriched population of exosomes can be obtained from a biological sample. For example, exosomes may be concentrated or isolated from a biological sample using size exclusion chromatography, density gradient centrifugation, differential centrifugation, nanomembrane ultrafiltration, immunoabsorbent capture, affinity purification, microfluidic separation, or combinations thereof.

Size exclusion chromatography, such as gel permeation columns, centrifugation or density gradient centrifugation, and filtration methods can be used. For example, exosomes can be isolated by differential centrifugation, anion exchange and/or gel permeation chromatography (for example, as described in U.S. Pat. Nos. 6,899,863 and 6,812,023), sucrose density gradients, organelle electrophoresis (for example, as described in U.S. Pat. No. 7,198,923), magnetic activated cell sorting (MACS), or with a nano-membrane ultrafiltration concentrator. Various combinations of isolation or concentration methods can be used.

Highly abundant proteins, such as albumin and immunoglobulin, may hinder isolation of exosomes from a biological sample. For example, exosomes may be isolated from a biological sample using a system that utilizes multiple antibodies that are specific to the most abundant proteins found in blood. Such a system can remove up to several proteins at once, thus unveiling the lower abundance species such as cell-of-origin specific exosomes.

This type of system can be used for isolation of exosomes from biological samples such as blood, cerebrospinal fluid, urine and/or saliva. The isolation of exosomes from a biological sample may also be enhanced by high abundant protein removal methods as described in Chromy et al. J. Proteome Res 2004; 3:1120-1127. In another embodiment, the isolation of exosomes from a biological sample may also be enhanced by removing serum proteins using glycopeptide capture as described in Zhang et al, Mol Cell Proteomics 2005; 4:144-155. In addition, exosomes from a biological sample such as urine may be isolated by differential centrifugation followed by contact with antibodies directed to cytoplasmic or anti-cytoplasmic epitopes as described in Pisitkun et al., Proc Natl Acad Sci USA, 2004; 101:13368-13373.

EXAMPLES

Example 1

Affinity Capture of Exosomes by Immuno-Magnetic Beads

Figure 1:
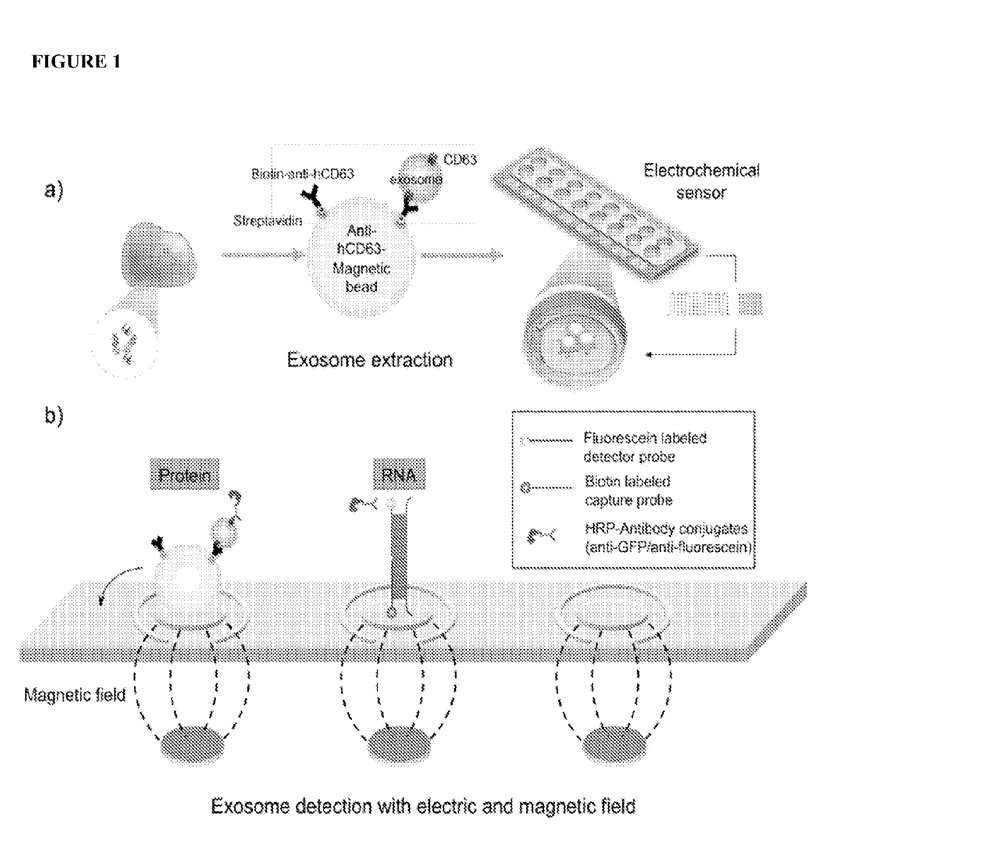
FIG. 1 depicts a schematic representation of the Electric Field Induced Release and Measurement (EFIRM) system. a) Anti-hCD63 antibodies were conjugated to magnetic beads, the beads were mixed with exosomes, and the mixture was transferred to the electrochemical sensor array for exosome extraction. b) A magnetic force was applied to collect the exosome-magnetic bead complexes onto the electrodes in the sensor array. An electric field was applied to induce release and then to measure both RNA and protein molecules. The magnetic beads were approximately 1-2 µm in diameter, as measured by transmission electron microscopy.

Effective exosome extraction requires efficiency and specificity. The technology described herein integrated exosome extraction enhanced with electrical field and magnetic bead techniques combined with simultaneous biomolecule release and detection. The detection was performed with amperometric electrochemical sensor technology(21) based on an array of 16 bare gold electrode chips (GeneFluidics, USA). The entire procedure is illustrated in FIG. 1.

Magnetic beads are an efficient tool for exosome extraction, because they facilitate exosome monitoring and detection of attached biomarkers. In this study, anti-human CD63 antibody (hCD63) attached to magnetic beads was used to capture exosomes that expressed membrane-bound CD63 (14) (FIG. 1).

To accomplish this, streptavidin-coated magnetic beads (Invitrogen, USA) were mixed with biotinylated anti-hCD63 (Ancell, USA) on a mixer for 30 min at room temperature. Then, 10 μL of H460 cell medium, serum, human saliva and murine saliva were incubated with the anti-hCD63-conjugated magnetic beads in casein-PBS (Invitrogen, USA). Murine saliva was used to demonstrate the specificity of the magnetic bead-based exosome extraction, which lacks the hCD63 protein. Samples were mixed for 2 h at room temperature to form exosome-magnetic bead complexes. Next, exosome-magnetic bead complexes were attracted onto the electrochemical sensor by applying an array of magnets. The unattached species were removed by washing.

Figure 2:
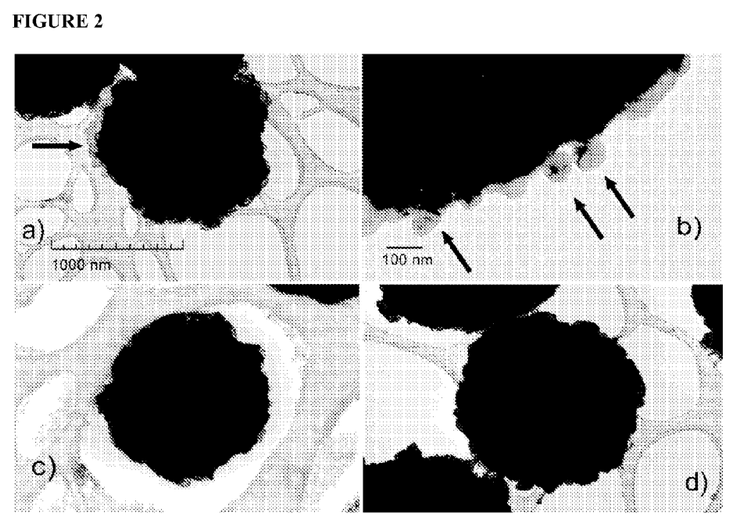
FIG. 2 depicts transmission electron microscopy (TEM) images of magnetic bead based exosome extraction. a) Exosomes (arrows) were extracted from human saliva with anti-hCD63-conjugated magnetic beads; b) Magnified view of human exosomes (arrows) on a bead; c) Mouse saliva after extraction with anti-hCD63-conjugated magnetic beads. No exosome is apparent. d) Human saliva after extraction with magnetic beads coated only with streptavidin (negative control).

Transmission electron microscopy (TEM) was used to examine exosomes after extraction with anti-hCD63 antibody-conjugated magnetic beads (FIG. 2a-b). For TEM measurements samples were loaded onto carbon-coated grids. Due to interference between the magnetic beads and the electric field of the electron microscope, specific grids were used to hold the magnetic beads. In addition, we used support film for TEM with a wide dynamic range to accommodate the size differences between the magnetic beads (1-2 μm diameter) and the exosomes (60-100 nm diameter). Lacey Formvar/Carbon with 200-mesh Copper (Ted-Peller, USA) was selected for the TEM support film. The samples were examined with a JEOL 100CX transmission electron microscope (JEOL USA, Inc. Peabody, Mass.).

The TEM images showed exosomes located on the surface of the magnetic beads. The sizes of the extracted particles ranged from 70-100 nm, consistent with the size distribution of typical exosomes(10, 14, 22) (FIG. 1b). The exosome extraction efficiency was approximately 85%, determined by comparing the levels of hCD63 found in extracted exosomes to the levels found in exosome-depleted human saliva. The TEM results showed no mouse-saliva exosomes attached to the beads (FIG. 1c). Furthermore, when beads were coated with streptavidin only, no exosomes were captured (FIG. 1d).

Example 2

Figure 3:
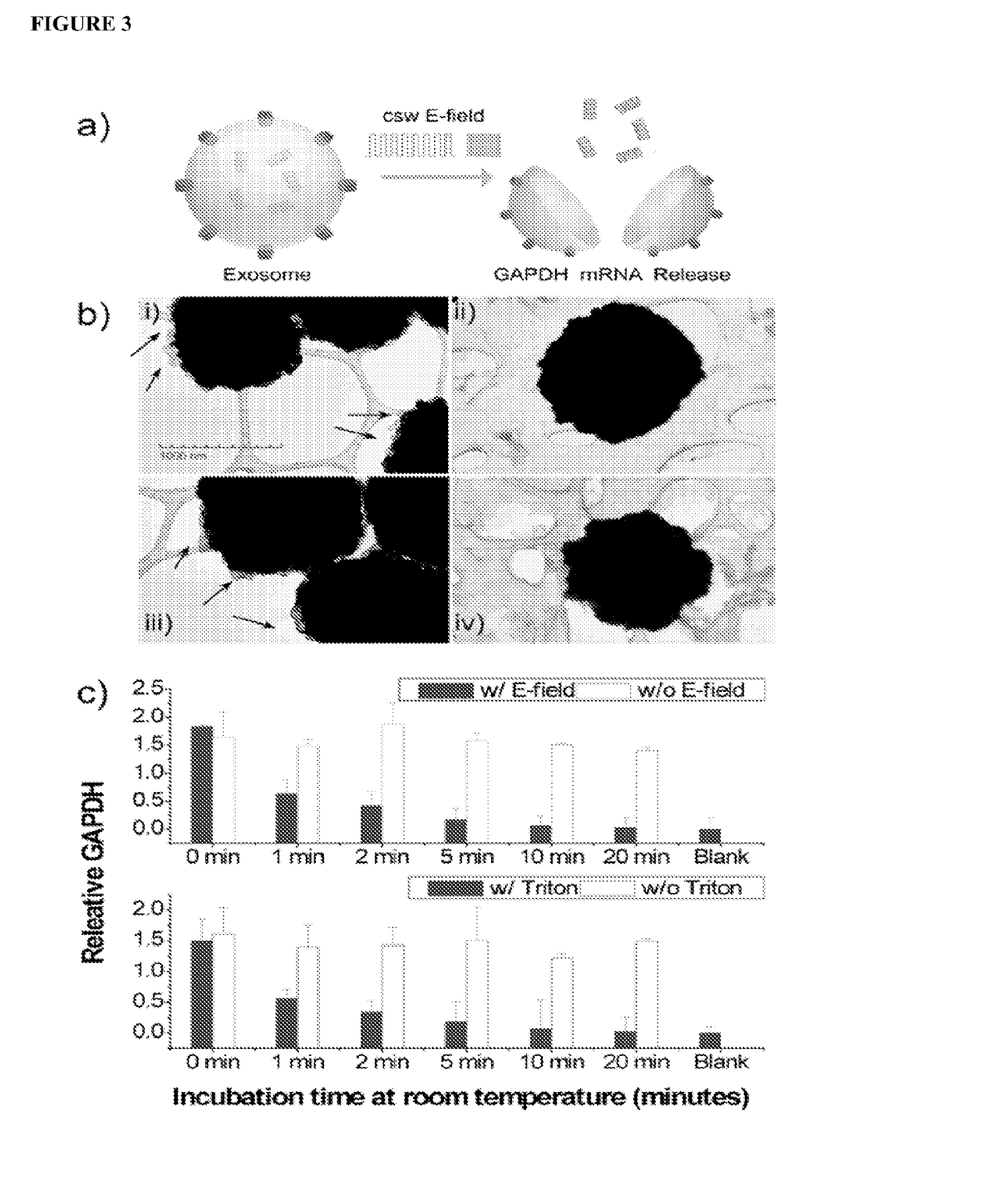

Release of Harbored mRNA from Human Saliva Exosomes Via Cyclic Square Wave (CSW) Electrical Field Triton™ X-100 has been shown to disrupt the integrity of salivary exosomes, but this leads to endogenous RNA degradation by RNases in the saliva matrix(18). Therefore, a rapid release process and immediate detection are necessary to effectively measure exosomal mRNA. A cyclic square wave electric field (csw E-field) was assessed to determine whether the csw E-field would facilitate the release and detection of RNA from human saliva exosomes (FIG. 3a). For comparison, the release efficiency was measured against Triton™ X-100 based lysis carried out on the same human saliva exosomes, captured by the same magnetic beads, and performed in parallel with the csw E-field assay.

Glyceraldehyde 3-phosphate dehydrogenase (GAPDH or G3PDH) mRNA is present in most exosomes. Therefore, measurement of GAPDH mRNA was utilized for comparing csw E-field to Triton™ X-100 based lysis.

For GAPDH mRNA detection, the electrodes were coated with a surface matrix of conducting polymer pyrrole. Then, the surface of the electrode was pre-coated with oligonucleotide capture probes with sequences specific for human GAPDH and a biotin label at the 5' end. The immobilization of the capture probe was carried out by applying a csw-E field for 20 cycles of 9 s at −300 mV followed by 1 s at +200 mV (200 s total)(21). After the exosome extraction step, the exosome-magnetic bead complex was collected onto the capture probe-coated electrode with an array of magnets placed underneath the electrochemical sensor. When loading the sample onto the electrode, 10 nM of detector probe (with a fluorescein-labeled 3' end) was mixed in with the exosome-magnetic bead complexes. The.csw E-field was then applied to release the harbored GAPDH mRNA from the exosomes. The csw-E field was 20 cycles of 9 s at −300 mV followed by 1 s at +200 mV (200 s total).

```
Capture probe:
                                    (SEQ ID NO: 1)
5'-Biotin-AGGTCCACCACTGACACGTTG Detector probe:
                                    (SEQ ID NO: 2)
5'-GCAGTGGGGACACGGAAGGCC-Fluorescein-3'
```

In parallel, samples from the same batches were lysed with 0.5% Triton™ X-100 (Sigma, USA) for 20 min at room temperature to compare release and protection efficiencies. The released mRNA hybridized with the oligonucleotide capture and detector probes. Then, we added 150 unit/ml of anti-fluorescein antibody conjugated to horseradish peroxidase (HRP; 1:1000 dilution; Roche, USA). Finally, the 3,3',5,5'-tetramethylbenzidine (TMB) substrate for horseradish peroxidase was loaded, and an amperometric signal was read out.

Exosome-magnetic bead complexes were examined by TEM before and after treatment with the csw E-field or Triton™ X-100 (FIG. 3b).

After both treatments, the exosomes on the beads disappeared. The levels of GAPDH mRNAs were measured at different time points by csw E-field after the application of electrical field or Triton™ X-100 (FIG. 3c). The results showed that the initially high GAPDH mRNA levels decreased gradually over the incubation time for both csw E-field and Triton™ X-100 disrupted samples. In contrast, the untreated exosomes (positive controls) maintained constant GAPDH mRNA levels during the experiment. These data demonstrate that both csw E-field and Triton™ X-100 detergent released the GAPDH mRNA from human saliva exosomes. With exposure to the salivary matrix, the signals dropped to less than 40% within one min. After 20 min, the readouts decreased down to the background level. The kinetics of the GAPDH mRNA signal decay demonstrates that the exosome protected and stabilized endogenous mRNA. Without the exosome protection, the GAPDH mRNA level rapidly decayed.

Example 3

Development of CSW-Field Technology to Simultaneously Detect Exosomal Surface Proteins and Harbored mRNA H460 cells were used to evaluate EFIRM technology for simultaneous measurements of an exosomal membrane protein (hCD63-GFP) and an exosomal mRNA (GAPDH). Purified hCD63-GFP exosomes were isolated by ultracentrifugation from medium conditioned by H460 cells. Exosomes were then incubated with magnetic beads coated with anti-hCD63. When the csw E-field was applied, both the GAPDH mRNA-DNA probe hybridization and the exosome-anti-GFP antibody binding were measured within minutes on the same detection chip.

The sensitivity of EFIRM for detecting exosomal GAPDH mRNA and hCD63-GFP protein was determined by benchmarking the results against conventional methods of Western blotting for detecting the hCD63-GFP protein and nested q-rtPCR for detecting the GAPDH RNA.

For the hCD63-GFP protein detection, there was no need to disrupt the endosome, because the protein was membrane-bound and the GFP portion was accessible to the medium. Therefore, the rabbit anti-GFP antibody conjugated to HRP (Invitrogen, USA) was mixed with the exosome-hCD63-magnetic bead complex in solution for 1 h at room temperature. After washing, the mixture was collected on the electrodes with the applied magnetic field. Then, the TMB substrate was added, and amperometric measurements were carried out. GFP protein levels are expressed relative to the negative control. This was calculated as the ratio between the sample and the blank casein PBS buffer.

Figure 4:
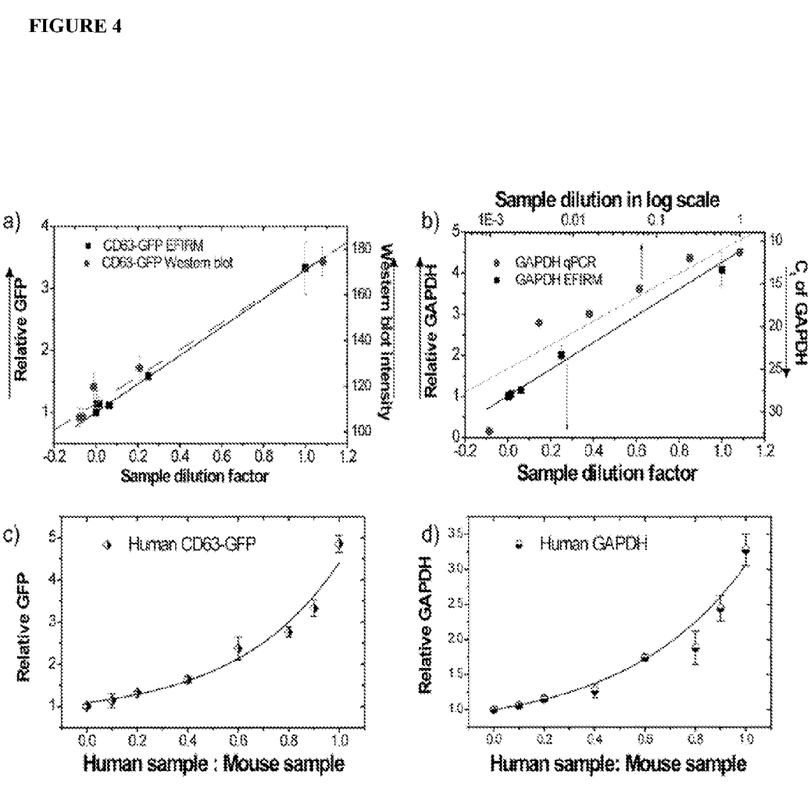
FIG. 4 depicts Western blot and qPCR measurements of hCD63-GFP protein and GAPDH mRNA in exosomes shed from H460 cells using E-field. a) Titration of the GFP moiety of hCD63-GFP by EFIRM and Western blotting. b) Titration of GAPDH mRNA by EFIRM and qPCR. Data in a) and b) are fitted by a linear model. The PCR readout is presented on a log scale. The human specificity of EFIRM measurements was tested by detecting human exosomal (c) CD63-GFP protein and (d) GAPDH mRNA in mixtures of endosomes from human lung cancer H460 cells and interfering exosomes from mouse Lewis lung carcinoma LL2/LLC1 cells. Both the GAPDH mRNA probe and the anti-GFP antibody were human-specific. Therefore, this assay tested whether mouse targets could interfere with detection of human targets.

Western blotting and EFIRM showed similar protein sensitivities at the same dilutions (FIG. 4a). The electrochemical level of GAPDH mRNA by EFIRM and the CT value on a log 10 scale from q-rtPCR also showed a similar trend, but different concentrations (FIG. 4b). These results demonstrated that the sensitivity of EFIRM was comparable to that of conventional methods for detecting both mRNA and GFP protein.

The specificity of EFIRM technology for detecting human protein (hCD63-GFP) and mRNA (hGAPDH mRNA) endosomal targets in the presence of interfering mouse exosomes. The detection probes were based on human-specific sequences for the GAPDH mRNA and the CD63 protein. We performed the EFIRM measurements of exosomal hCD63-GFP protein and GAPDH mRNA on mixtures of human and mouse exosomes at different volume ratio. The corresponding electrochemical signals are presented in FIGS. 4c and 4d vs the ratio between human and mouse exosome. The pure human exosomes (ratio=1) showed higher signal intensities than the pure mouse exosomes (ratio=0) (FIGS. 4c and d). Even when the human exosomes were highly outnumbered by mouse exosomes (human exosome: mouse exosome=0.2), the signal remained above 2 standard deviations from the pure mouse exosome sample. This result showed that the EFIRM technology was highly specific in the detection of both human GAPDH mRNA and hCD63-GFP protein.

Example 4

EFRIM Technology for Detecting Exosomal hCD63-GFP in Body Fluids

EFIRM successfully detected exosomal surface protein and harbored mRNA simultaneously, whether EFIRM technology could be applied to an in vivo system was therefore tested. Nude mice were implanted with the human lung cancer cell line H460, which expressed hCD63-GFP.

Male athymic BALB/c nude mice were obtained from Charles River (USA) and weighed 20-22 g at the beginning of the experiments. The mice were housed in sterilized, filter-topped cages and maintained under sterile conditions. Each mouse received an injection of $1 \times 10^6$ H460 cells that expressed hCD63-GFP (n=9) or 100 µl (n=11) saline in the left chest cavity. Briefly, the mice were anesthetized with 1-3% isoflurane in oxygen with a precision vaporizer. The mice were then placed in a right lateral, decubitus position and a suspension of H460 cells or saline was injected (100 µl) slowly into the left intercostal space at the dorsal mid-axillary line, just below the inferior border of the scapula with a 30-ga needle attached to a 1-cc syringe. The needle was advanced approximately 5 mm through the chest wall into the pleural space. After injection, the needle was retracted, and mice were turned to the left lateral decubitus position for recovery. After 20 days, mice reached a moribound condition, and serum and saliva was collected before euthanization.

Figure 5:
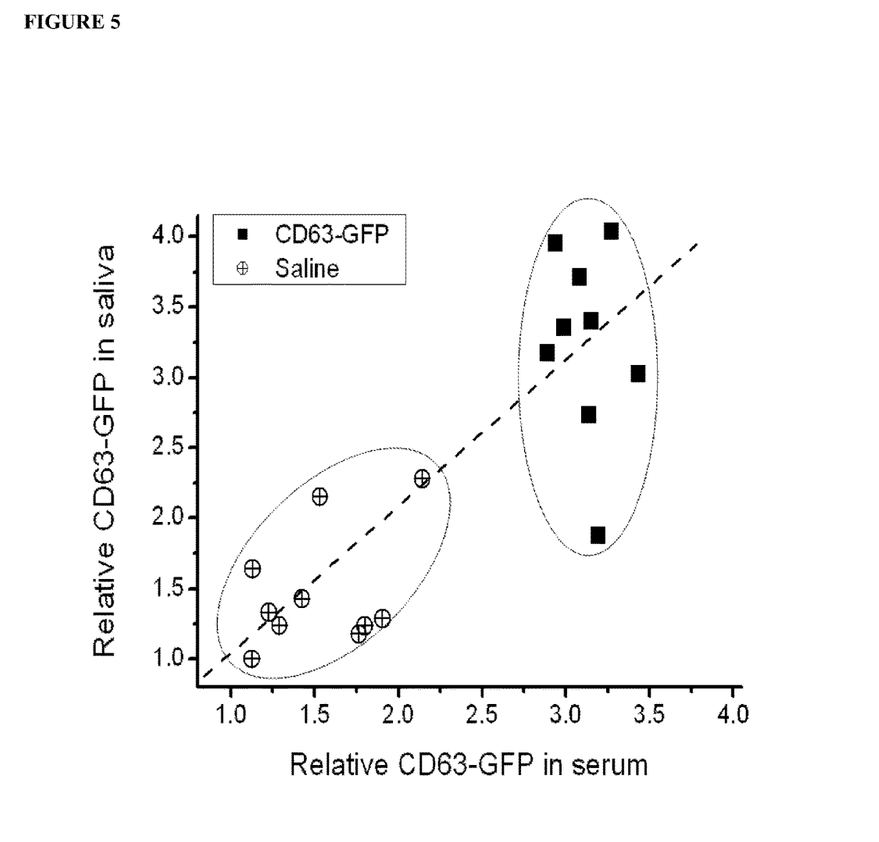
FIG. 5 depicts the correlation between human CD63-GFP levels in saliva and serum measured with EFIRM technology. Samples are from mice that had been injected with a human lung cancer cell line that expressed CD63-GFP (solid squares) or with saline alone (cross and circles). Each point represents the ratio of electrochemical current readings from serum (X-axis) and saliva (Y-axis) relative to the blank control reading. Relative values close to 1 indicate low hCD63-GFP levels, because there was a small difference between the signal and the blank control (casein PBS). The linear regression is indicated with the dashed line (R=0.77).

EFIRM was then to measure hCD63-GFP positive exosomes in saliva and serum. FIG. 5 shows the correlation between exosomal hCD63-GFP levels in saliva and serum. All 20 samples had measurable hCD63-GFP levels by EIFRM in both serum and saliva. Data points close to the line (slope=1) indicate that the serum and saliva had similar protein concentrations; data points below the line indicate a higher signal in serum than in saliva, and vice versa. Therefore, the human CD63-GFP-exosome levels from serum and saliva correlated well (R=0.77) in the 20 mouse samples (both serum and saliva were measured for each mouse). Furthermore, the mice injected with hCD63-GFP and those injected with saline (control group) showed significant differences in the hCD63-GFP positive exosomes in both serum and saliva. The low relative values (1 was the same as the blank control) measured in the saline group suggested that the saline injection did not generate high GFP signals in either serum or saliva. The detection required only 10 µl of raw sample in an on-site measurement. The time from the raw sample loading to detection was approximately 3 h.

REFERENCES

1. Rosell R, Wei J, & Taron M (2009) Circulating MicroRNA Signatures of Tumor-Derived Exosomes for Early Diagnosis of Non-Small-Cell Lung Cancer. Clinical Lung Cancer 10, 8-9.

2. Fevrier B & Raposo G (2004) Exosomes: endosomal-derived vesicles shipping extracellular messages. Current Opinion in Cell Biology 16, 415-421.

3. Valadi H, Ekstrom K, Bossios A, Sjostrand M, Lee J J, & Lotvall J O (2007) Exosome-mediated transfer of mRNAs and microRNAs is a novel mechanism of genetic exchange between cells. Nature Cell Biology 9, 654-U672.

4. Smalheiser N R (2007) Exosomal transfer of proteins and RNAs at synapses in the nervous system. Biology Direct 2.

5. van Niel G, Porto-Carreiro I, Simoes S, & Raposo G (2006) Exosomes: A common pathway for a specialized function. Journal of Biochemistry 140, 13-21.

6. Stoorvogel W, Kleijmeer M J, Geuze H J, & Raposo G (2002) The biogenesis and functions of exosomes. Traffic 3, 321-330.

7. Taylor D D & Gercel-Taylor C (2010) MicroRNA signatures of tumor-derived exosomes as diagnostic biomarkers of ovarian cancer (vol 110, pg 13, 2008). Gynecologic Oncology 116, 153-153.

8. Pisitkun T, Shen R F, & Knepper M A (2004) Identification and proteomic profiling of exosomes in human urine. Proc Natl Acad Sci USA 101, 13368-13373.

9. Miranda K C, Bond D T, McKee M, Skog J, Paunescu T G, Da Silva N, Brown D, & Russo L M (2010) Nucleic acids within urinary exosomes/microvesicles are potential biomarkers for renal disease. Kidney International 78, 191-199.

10. Johansson S M, Admyre C, Rahman Q K, Filen J J, Lahesmaa R, Norman M, Neve E, Scheynius A, & Gabrielsson S (2006) Exosome-like vesicles in human breast milk. Journal of Immunology 176, S184-S184.

11. Sharma S, Rasool H I, Palanisamy V, Mathisen C, Schmidt M, Wong D T, & Gimzewski J K (2010) Structural-mechanical characterization of nanoparticle exosomes in human saliva, using correlative AFM, FESEM, and force spectroscopy. ACS Nano 4, 1921-1926.

12. Palanisamy V, Sharma S, Deshpande A, Zhou H, Gimzewski J, & Wong D T (2010) Nanostructural and Transcriptomic Analyses of Human Saliva Derived Exosome. Plos One 5.

13. Gibbings D J, Claudo C, Erhardt M, & Voinnet O (2009) Multivesicular bodies associate with components of miRNA effector complexes and modulate miRNA activity. Nat Cell Biol 11, 1143-1149.

14. Schorey J S & Bhatnagar S (2008) Exosome function: From tumor immunology to pathogen biology. Traffic 9, 871-881.

15. Schmid M & Jensen T H (2008) The exosome: a multipurpose RNA-decay machine. Trends in Biochemical Sciences 33, 501-510.

16. Houseley J, LaCava J, & Tollervey D (2006) RNA-quality control by the exosome. Nature Reviews Molecular Cell Biology 7, 529-539.

17. Chen C, Skog J, Hsu C H, Lessard R T, Balaj L, Wurdinger T, Carter B S, Breakefield X O, Toner M, & Irimia D (2010) Microfluidic isolation and transcriptome analysis of serum microvesicles. Lab Chip 10, 505-511.

18. Park N J, Li Y, Yu T W, Brinkman B M N, & Wong D T (2006) Characterization of RNA in saliva. Clin. Chem. 52, 988-994.

19. Wei F, Qu P, Zhai L, Chen C, Wang H, & Zhao X S (2006) Electric potential induced dissociation of hybridized DNA with hairpin motif immobilized on silicon surface. Langmuir 22, 6280-6285.

20. Wei F, Liao W, Xu Z, Yang Y, Wong D T, & Ho C M (2009) Bio/abiotic interface constructed from nanoscale DNA dendrimer and conducting polymer for ultrasensitive biomolecular diagnosis. Small 5, 1784-1790.

21. Wei F, Patel P, Liao W, Chaudhry K, Zhang L, Arellano-Garcia M, Hu S, Elashoff D, Zhou H, Shukla S, et al. (2009) Electrochemical sensor for multiplex biomarkers detection. Clin Cancer Res 15, 4446-4452.

22. Ogawa Y, Kanai-Azuma M, Akimoto Y, Kawakami H, & Yanoshita R (2008) Exosome-like vesicles with dipeptidyl peptidase IV in human saliva. Biol Pharm Bull 31, 1059-1062.

23. Park N J, Zhou H, Elashoff D, Henson B S, Kastratovic D A, Abemayor E, & Wong D T (2009) Salivary microRNA: discovery, characterization, and clinical utility for oral cancer detection. Clin Cancer Res 15, 5473-5477.

24. Gonzalez-Begne M, Lu B, Han X, Hagen F K, Hand A R, Melvin J E, & Yates J R (2009) Proteomic analysis of human parotid gland exosomes by multidimensional protein identification technology (MudPIT). J Proteome Res 8, 1304-1314.

25. Denzer K, Kleijmeer M J, Heijnen H F, Stoorvogel W, & Geuze H J (2000) Exosome: from internal vesicle of the multivesicular body to intercellular signaling device. J Cell Sci 113 Pt 19, 3365-3374.

26. Caby M P, Lankar D, Vincendeau-Scherrer C, Raposo G, & Bonnerot C (2005) Exosomal-like vesicles are present in human blood plasma. Int Immunol 17, 879-887.

27. Kesimer M, Scull M, Brighton B, DeMaria G, Burns K, O'Neal W, Pickles R J, & Sheehan J K (2009) Characterization of exosome-like vesicles released from human tracheobronchial ciliated epithelium: a possible role in innate defense. FASEB J 23, 1858-1868.

28. Wubbolts R, Leckie R S, Veenhuizen P T, Schwarzmann G, Mobius W, Hoernschemeyer J, Slot J W, Geuze H J, & Stoorvogel W (2003) Proteomic and biochemical analyses of human B cell-derived exosomes. Potential implications for their function and multivesicular body formation. J Biol Chem 278, 10963-10972.

29. Sugioka H (2011) Asymmetrical reverse vortex flow due to induced-charge electro-osmosis around carbon stacking structures. Physical Review E 83.

30. Liu C H, Puttaswamy S V, Sivashankar S, Yeh C H, & Chen R J (2010) Electrodynamically actuated on-chip flow cytometry with low shear stress for electro-osmosis based sorting using low conductive medium. Microelectronic Engineering 87, 2582-2591.

31. Wong P K, Wang T H, Deval J H, & Ho C M (2004) Electrokinetics in micro devices for biotechnology applications. Ieee-Asme Transactions on Mechatronics 9, 366-376.

32. Chen T-H, Wei F, & Ho C M (2009) Near-field ion flow for molecular scale manipulation. Solid-State Sensors, Actuators and Microsystems Conference, 2009. TRANSDUCERS 2009. International 421-424.

All references cited herein are hereby incorporated by reference herein in their entirety and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments described herein are offered by way of example only, and the application is to be limited only by the terms of the appended claims, along with the full scope of equivalents to which the claims are entitled.

What is claimed is:

1. A method for detecting a biomarker present in an exosome, the method comprising:
   (a) providing a biological fluid comprising exosomes;
   (b) extracting exosomes from the biological fluid to form an enriched exosome composition;
   (c) contacting the enriched exosome composition with a detection reagent that specifically binds to the biomarker;
   (d) releasing the biomarker from the enriched exosome composition by applying an electrical field to the enriched exosome composition in the presence of the detection reagent, wherein the electrical field is sufficient to lyse the exosomes, thereby release the biomarker from the enriched exosome composition;
   (e) detecting an interaction between the released biomarker and the detection reagent.

2. The method of claim 1, wherein the biomarker is selected from the group consisting of a protein, a nucleic acid, and an mRNA.

3. The method according to claim 1, wherein the biological fluid is selected from the group consisting of saliva, whole blood, blood plasma, blood serum, amniotic fluid, bile, colostrum, breast milk, cerebrospinal fluid (CSF), lymph, gastric acid, nasal mucus, pleural fluid, semen, tears, and urine.

4. The method according to claim 1, wherein the step of extracting exosomes from the biological fluid comprises:
   (1) contacting the biological fluid with an exosome extraction reagent that specifically binds to a surface-exposed exosome marker to form a complex between the exosome and the exosome extraction reagent; and
   (2) separating the complex formed between the exosome and the exosome extraction reagent from the biological fluid.

5. The method of claim 4, wherein the surface-exposed exosome marker is CD63.

6. The method of claim 4, wherein the exosome extraction reagent comprises an antibody or a exosome-specific lectin.

7. The method according to claim 4, wherein the exosome extraction reagent comprises a bead attached to a first affinity moiety that specifically binds to a surface-exposed exosome marker.

8. The method of claim 7, wherein the bead is a magnetic bead.

9. The method according to claim 1, wherein the detection reagent comprises a second affinity moiety immobilized to a solid phase, wherein the second affinity moiety specifically binds to the biomarker.

10. The method of claim 9, wherein the second affinity moiety comprises an antibody or a nucleic acid.

11. The method according to claim 9, wherein the solid phase comprises an electrochemical sensor.

12. The method according to claim 1, wherein the absolute value of the maximum voltage of the electric field does not exceed 1 volt or 500 millivolt (mV).

13. The method according to claim 1, wherein the electric field is applied for less than 300 seconds or is applied for 200±30 seconds.

14. The method according to claim 1, wherein the electric field is a non-uniform electric field.

15. The method of claim 14, wherein the non-uniform electric field is a cyclic square wave electrical field (csw E-field).

16. The method of claim 15, wherein the csw E-field comprises 15 cycles of −300±50 mV for 9±2 seconds followed by 200±50 mV for 1±0.5 second.

17. The method of claim 16, wherein the csw E-field comprises 20 cycles of −300 mV for 9 seconds followed by 200 mV for 1 second.

18. A method for detecting a biomarker present in an exosome, the method comprising:
- (a) providing a biological fluid comprising exosomes;
- (b) contacting the biological fluid with an exosome extraction reagent to form a complex between the exosome and the exosome extraction reagent, the exosome extraction reagent comprising a first affinity moiety bound to a magnetic bead, wherein the first affinity binding moiety specifically binds to a surface-exposed exosome marker;
- (c) separating the complex formed between the exosome and the exosome extraction reagent from the biological fluid;
- (d) contacting a solid phase with the complex formed between the exosome and the exosome extraction reagent, the solid phase comprising a first contact region under the influence of a magnetic field, a second contact region, and a detection reagent immobilized at the second contact region, the detection reagent comprising a second affinity moiety that specifically binds to the biomarker;
- (e) immobilizing the complex formed between the exosome and the exosome extraction reagent at the first contact region;
- (f) releasing the biomarker from the exosome by applying an electrical field to the immobilized complex formed between the exosome and the exosome extraction reagent at the first contact region, wherein the electrical field is sufficient to lyse the exosome, thereby releasing the biomarker from the exosome; and
- (e) detecting an interaction between the biomarker and the detection reagent.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Homo sapiens

<400> SEQUENCE: 1
aggtccacca ctgacacgtt g                                          21

<210> SEQ ID NO 2
<211> LENGTH: 21
<212> TYPE: DNA
<213> ORGANISM: Homo sapiens

<400> SEQUENCE: 2
gcagtgggga cacggaaggc c                                          21